United States Patent
Effing et al.

(10) Patent No.: US 9,271,873 B2
(45) Date of Patent: *Mar. 1, 2016

(54) FILM DRESSING COMPRISING AN APPLICATION AID

(75) Inventors: Jochem Effing, Kelkheim-Fischbach (DE); Axel Eckstein, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 471 days.

This patent is subject to a terminal disclaimer.

(21) Appl. No.: 11/849,289

(22) Filed: Sep. 2, 2007

(65) Prior Publication Data

US 2008/0281245 A1    Nov. 13, 2008

Related U.S. Application Data

(63) Continuation of application No. PCT/EP2006/001732, filed on Feb. 24, 2006.

(30) Foreign Application Priority Data

Mar. 3, 2005  (DE) .......................... 10 2005 009 635

(51) Int. Cl.
*A61F 13/00*  (2006.01)
*A61F 13/02*  (2006.01)

(52) U.S. Cl.
CPC ..................................... *A61F 13/02* (2013.01)

(58) Field of Classification Search
CPC ....... A61F 13/02; A61F 13/51; A61F 13/023; A61F 13/0236; A61F 13/024
USPC ............ 602/43, 58, 386, 48, 52, 54, 57, 904, 602/41, 42; 604/304, 307, 308, 386
See application file for complete search history.

(56) References Cited

U.S. PATENT DOCUMENTS

| | | | | |
|---|---|---|---|---|
| 4,753,232 | A * | 6/1988 | Ward ............................... | 602/52 |
| 5,628,724 | A * | 5/1997 | DeBusk et al. .................. | 602/58 |
| 5,960,795 | A * | 10/1999 | Schultz .......................... | 128/888 |
| 5,985,395 | A * | 11/1999 | Comstock et al. ............ | 428/40.1 |
| 6,297,422 | B1 * | 10/2001 | Hansen et al. .................. | 602/57 |
| 7,723,561 | B2 * | 5/2010 | Propp ............................ | 602/58 |

FOREIGN PATENT DOCUMENTS

| | | | |
|---|---|---|---|
| EP | 0401949 | A2 * | 5/1989 |
| EP | 0401949 | A2 * | 5/1990 |
| EP | 401949 | A2 * | 12/1990 |
| JP | 03-007153 | | 6/1989 |
| JP | 07-38138 | | 12/1993 |

* cited by examiner

*Primary Examiner* — Victoria J Hicks
(74) *Attorney, Agent, or Firm* — Brinks Gilson & Lione

(57) ABSTRACT

The present disclosure relates to a film dressing having a polymer film and an application system for permitting an improved ease of use of said film dressing. The application system is located on the first side of the polymer film and has at least one first and one second supporting film. At least one first grip strip is formed on the first supporting film and at least one second grip strip is formed on the second supporting film. At least the first grip strip has a grip surface that enables the grip strip to be grasped and the first grip strip at least partially overlaps the second grip strip.

16 Claims, 4 Drawing Sheets

FILM DRESSING COMPRISING AN APPLICATION AID

CROSS-REFERENCE TO RELATED APPLICATIONS

This application is a continuation of International Application No. PCT/EP2006/001732 filed on Feb. 24, 2006, which claims the benefit of German Patent Application No. 10 2005 009 635.2, filed Mar. 3, 2005. The disclosures of the above applications are incorporated herein by reference.

FIELD

The present disclosure relates to a film dressings and in particular an application system to improve the ease of use of the film dressing.

BACKGROUND

The statements in this section merely provide background information related to the present disclosure and may not constitute prior art.

Application aids for adhesive bandages or wound dressings have been known for quite some time. These application aids are particularly being used in film or foil dressings. Film dressings are thin, usually transparent, semi-permeable films or foils out of polymer material. The semi-permeability of the film prevents the invasion of bacteria or moisture while allowing a sufficient exchange of oxygen and condensation between the skin to be covered and the outer surroundings of the film dressing. These film or foil dressings are used in multiple applications, for example as incision film for the sterile covering of surgery wounds, as water-proof cover of wound dressings that absorb exudates as well as for the positioning of syringes or catheters. Due to the minimal thickness of these films or foils and their respective instability, these film dressings are equipped with various application aids. Most of these application aids use an additional supporting layer, which is removed during or after the application of the film dressing.

The patent literature has also known film wound dressings for quite some time. EP 81 990 B1 thus describes an adhesive wound dressing that consists of a thin polymer film. This polymer film is coated on one side with an adhesive material that adheres to the skin, which in turn is covered with a removable layer. On the other side, which during application is opposite of the body, the polymer film also has an easily removable support layer to improve the ease of use, which consists of a fibrous material, for example, a non-transparent non-woven material. This support layer has the same size as the polymer film.

EP 690 706 B1 describes an adhesive wound dressing, which has a carrying layer to aid the ease of application of a polymer film, which is comprised by a wound dressing. This carrying layer completely covers the polymer film and can be removed from the polymer film in two steps. For this purpose, a center section is removed from the carrying layer, whereas in the next step a frame section is removed. The fact that it is difficult for the user to grasp the carrying layer of this wound dressing is unfavorable.

Additionally, EP 951 263 B1 describes an adhesive film dressing, where at least one two-part removable protective layer covers the adhesive side and where its non-adhesive second side comprises a one-part support layer. The support layer in this film dressing is hinge-like attached to the protective layer on two opposite sides so that the support layer is removed simultaneously with the protective layer.

EP 473 918 B1 describes a film dressing that comprises a one-sided supporting film, which in turn has one grip strip on each of the two opposite sides. This position of the grip strips has the disadvantage that there is no pre-determined direction for removing the supporting film.

EP 985 931 A1 describes a dressing material on a film basis, which comprises a non-adhesive gripper in the peripheral area of the film. The non-adhesive side of the film comprises a one-part support layer, which is equal to the size of the film and comprises at least one grip strip. By pulling the gripper in the direction of the adhesion, the applied film can again be removed painlessly.

The European patent specification EP 630 628 B1 established a film dressing that comprises for the ease of application a two-part supporting film. This supporting film is larger than the film to be applied and completely covers it. In order to remove the supporting film, the supporting film comprises an additional adhesive removal strip, which is positioned above the intersection line of the supporting film and for handling purposes has two non-adhesive peripheral areas that serve as grip strips. This additional removal strip serves to remove only a portion of the supporting film, whereas the second part of the supporting film remains on the polymer film.

WO 97/25012 A1 suggests a film dressing which is provided either continuously or only on two opposing peripheral areas of the film with a two-part supporting layer. If the supporting film is continuously attached to the film dressing, then gripper supports may be positioned on the supporting film. The adhesive protective layer opposite of the supporting layer is divided into three sections.

These protective rights present various alternative solutions to film and foil dressings with various application systems. The film dressings which have been suggested as a solution in these protective rights are viewed in part as too complicated in their construction and too complicated in their application. Furthermore, the film dressings with application aids suggested in these protective rights all exhibit a rigidity which is considered too high in respect of the very flexible polymer film that is actually to be applied. This flexibility of the film dressings is necessary, however, to apply the polymer films, which are actually to be applied, accurate and wrinkle-free.

SUMMARY

The "Application system" according to the present disclosure shall include everything that permits the improved ease of use of the polymer film and comprises at least two supporting films and in addition to these supporting films comprises at least two grip strips which are formed on said supporting films. "Forming" in this context shall mean the combining of two similar or two different materials which are separable or inseparable with one another by means of adhesives, pressure, thermal energy, ultra-sonic applications or other procedures. The grip strip is therefore presently always an additional material component, whereas the grip strip can always be removed from the polymer film with at least one supporting film. Furthermore, for the ease of understanding in the context of the present disclosure, a film or polymer film shall always refer to the film or polymer film actually to be applied, for example a wound dressing; in contrast, a film or polymer and/or supporting film shall always refer to a part of the application system; that means the difference between film and foil in this case only refers to the function of the components. No distinction shall be made in respect of the material between the terms of film and foil.

This positioning of the grip strips provides the user with a particularly simple means to manipulate in each case only the upper-most first grip strip as the first grip strip and therefore remove a first supporting film as the first film from the polymer film. The user is only able to remove a second supporting film in the second step with the aid of a second grip strip. This determines a succession in the removal of the supporting films and provides a particularly safe means of handling the film dressing.

In a first preferred embodiment of a film dressing according to the present disclosure, the first grip strip comprises a grip area that can be determined by the user when grasping said grip strip, preferably designed as a rear grip device of at least 2 cm$^2$, particularly at least 5 cm$^2$ and especially preferred of at least 7 cm$^2$. It is particularly intended that the first grip strip completely overlap the second grip strip. It has been proven particularly safe to manipulate when the first grip strip comprises an exposed grip area of at least 2 cm$^2$, particularly at least 4 cm$^2$ and especially preferred of at least 6 cm$^2$. This exposed grip area is in this case the section of the grip area that marginally protrudes the second grip strip.

In another preferred embodiment of a film dressing according to the present disclosure, the second grip strip comprises a grip area that can be determined by the user when grasping said grip strip, preferably designed as rear grip device of at least 2 cm$^2$, particularly at least 3 cm$^2$ and especially preferred of at least 4 cm$^2$.

Another version of the present disclosure illustrates that the area of the polymer film, which is covered by the supporting films, is smaller than the first layer of the polymer film. The polymer film therefore has at least one area without a supporting film. The film dressing has particularly in this embodiment two or more supporting films, where their combined contact area is less than about 97% and particularly less than about 94% of the first layer of the polymer film to be applied.

The advantage of such a film dressing with at least one area without a supporting film is the fact that this area of the polymer film, which is not covered by a supporting film, due to the higher flexibility in comparison to the polymer film with supporting film can function as a joint during the application of the film dressing. A relatively rigid material can therefore be used as supporting film, which at the same time assures precise application. In a familiar supporting film consisting of multiple parts which completely covers the polymer film, the choice of supporting materials must be limited to relatively flexible materials in order to assure precise application of the polymer film.

In particular, a first area that is not covered by the supporting films can be positioned at the edge of the polymer film. An edge shall be understood as every section of an area, which extends from the border of an area into the interior of an area, whereas the area extension of the edge is smaller than about 50% of the entire area. This provides a film dressing, which favorably comprises an area, which comprises a flexibility that is pre-determined by the polymer film itself and assures an easy first positioning of the film to be applied, where at the same time the supporting films assure secure handling in the additional areas. It has been proven that it is particularly easy and safe to manipulate when one of the supporting films has in at least one point of its outer edge a distance from the outer edge of the polymer film of at least about 2 mm, particularly at least about 3 mm and especially of at least about 5 mm. Particularly preferred is a distance, which has in each point of the edge of the supporting film an equal distance of at least about 2 mm, particularly at least about 3 mm and especially at least about 5 mm to the outmost edge of the polymer film.

Another embodiment of the present disclosure illustrates that a grip strip at least partially overlaps an area of the polymer film that is not covered by the supporting films. It is also possible that the grip strip completely overlaps the area that is not covered by the supporting film. The application system can furthermore comprise the same size as the polymer film. The same size in this context refers to a size in respect of the contact surface, that means the circumferential limitations of the application system and the polymer film are aligned. Due to the same size of the application system and the polymer film, and due to the fact that the grip strip is only formed on the supporting film and is not connected to the polymer film, it is assured that in addition to the previously described high flexibility within the area not covered by the supporting film the entire film is covered as well and therefore also completely protected during its application.

In a further development of the spirit of the disclosure, the film dressing can comprise a first area between the supporting films which is not covered by the supporting films. The distance between both supporting films is preferably in each point at least about 2 mm, particularly about 3 mm and especially about 5 mm. Particularly preferred is an application system that has two supporting films, which in each point have the same distance to one another. It has been proven particularly safe to manipulate when the first grip strip completely overlaps the uncovered area of the polymer film as well as the second grip strip. This assures that in each case, the user can only manipulate the upper-most first grip strip as the first grip strip and thereby removes the first supporting film from the polymer film and the entire polymer film is covered by the application system.

If the film dressing comprises an application system with two supporting films and a first area without supporting film is intended between the supporting films, separate from this first non-covered area a second area can be designed which is also not covered by a supporting film. This second area can furthermore preferably be covered by a grip strip. Another design is also possible where this second area is covered neither by a supporting film nor by a grip strip. In the preferred version, this second non-covered area of the polymer film is positioned at one edge of the film dressing. The film dressing in this manner comprises a joint within the dressing as well as an area for its initial positioning.

If an application system is intended that comprises more than two supporting films, then each supporting film can be assigned to a grip strip. In a particularly preferred embodiment, two supporting films may be assigned to one grip strip. In particular, in one film dressing with three supporting films, two supporting films can be assigned to one grip strip. With this arrangement and/or assignment of the grip strips on the supporting films, two separate supporting films can be removed in one-step. Transparent or translucent film materials are particularly intended as supporting films. However, opaque or non-transparent film materials can be used alternatively. Used as supporting film are particularly those films that are manufactured from polyester, polyethylene, polypropylene, polyvinylchloride, polystyrene, polyamide, polycarbonate, cellulose ester, ethylene vinyl acetate, polyvinyl acetate, polyvinyl alcohol and/or combinations thereof. Particularly preferred are supporting films from transparent polyester or polyethylene or polypropylene. At the same time, it has been proven to be particularly preferable when the thickness of the supporting films are adjusted to comprise a thickness of about 15 to about 80 µm, particularly of about 20 to about 60 µm and especially of about 20 to about 40 µm.

In order to manufacture a grip strip, the same materials can be used that are used for the supporting films. In a particularly preferred embodiment, the grip strip is manufactured from a film material that is more flexible than the supporting film. If an application system is intended that comprises two or more supporting films and two or more grip strips, then all grip strips are manufactured from one material that is more flexible than any supporting film. This assures that the grip strips are very easy to grasp. In another particularly preferred embodiment with two grip strips, it is intended that the grip strip of the first supporting film is more flexible than the grip strip of the second supporting film. At the same time, it is also advantageous if the second grip strip completely overlaps the first grip strip.

An activation device can be provided in addition to a system with two grip strips that is positioned between the first and the second grip strip. This activation device can for example be an additional adhesive strip with an adhesive strength that is different for the contact surface of each side. When using such film dressings, one first grip strip, which is positioned above the second grip strip, can for example be grasped and with this grip strip the activation device and one supporting film can be removed from the polymer film, whereas the second grip strip is hence simultaneously activated and/or lifted up in such manner that it is easier for the user to grasp.

In a film dressing according to the present disclosure, polymer films can be particularly used that are highly permeable to condensation. For this, those films are particularly practical that are manufactured from polyurethane, polyether urethane, polyester urethane, polyether-polyamide urethane, polyacrylate or polymethacrylate. Particularly preferred as polymer film is a polyurethane film, polyester urethane film or polyether urethane film. Most particularly preferred are also such polymer films that have a thickness of about 15 to about 50 µm, particularly of about 20 to about 40 µm and especially of about 25 to about 30 µm. The condensation permeability of the polymer film in a film dressing according to the present disclosure is preferably at least about 750 $g/m^2/24$ hrs., particularly at least about 1000 $g/m^2/24$ hrs., and especially at least about 2000 $g/m^2/24$ hrs. (measured according to DIN 13726).

An adhesive can be applied on the second side which is opposite of the application system of the polymer film to be applied. This application can be continuously as well as discontinuously or only in certain areas. The applied adhesive can be a common adhesive, particularly an acryl adhesive or a pressure-sensitive adhesive on polyurethane basis. Preferred are gel adhesives, especially on polyurethane basis, particularly water-based polyurethanes. Especially preferred are hydro-gel adhesives, particularly on water-based acrylics.

In the preferred version, the basic weight of the adhesive is about 20-100 $g/m^2$, particularly about 35-50 $g/m^2$, whereas the adhesive can be applied discontinuously, but preferably continuously.

The condensation permeability of the polymer film which has been prepared with adhesive is preferably at least about 1000 $g/m^2/24$ hrs, particularly preferred about 1200 $g/m^2/24$ hrs, and especially preferred at least about 2000 $g/m^2/24$ hrs. (measured according to DIN EN 13726).

According to a development of the present disclosure, the film dressing on the second side of the polymer film opposite of the application system can be continuously coated with an adhesive and the adhesive can be protected with a cover paper. Any commonly available silicone paper or film as well as a paper or film coated with a fluoride combination can be used as a cover layer.

If the film dressing is to be produced as a wound dressing, according to a further embodiment a wound pad or wound cushion must be positioned on the second side of the polymer film, which during the application is positioned towards the body. Such film dressing is particularly suited as wound cover when the wound pad or cushion is adhesively attached to the polymer film. This wound cushion can be made of fleece, therefore a non-woven material. This fleece is preferably a hydrophilic fibrous material such as cotton, viscose, cellulose and polyester or their combinations, preferably with hydrophilic polyethylene or polypropylene.

Instead of the wound cushion or in addition to the wound cushion, the film dressing can on the second side of the polymer film, which during the application is positioned towards the body, particularly be provided with a layer that promotes the healing of the wound. A layer that promotes the healing of the wound means any layer that is used for treatment on moist wounds. Particularly preferred here are hydrogels based on polyurethane, acrylics or water-soluble celluloses or combinations thereof, which comprise water content of at least about 50% in relation to the total weight of the hydrogel. These hydrogels can be applied directly to the wound cushion as well as to the second side of the polymer film.

In order to provide a film dressing that is safe to handle, the used materials must be precisely in coordination with one another. The used materials must be particularly coordinated in respect of their release characteristics. These release characteristics that are adjustable with additional means are based on the forces that exist between the two used materials. A targeted surface treatment of a material can for instance be used to adjust an attracting of rejecting effect in relation to a second material, which is to be joined with the first material. A surface treatment, which causes an attracting effect between two materials, can for instance follow due to an adhesive coating, a static charge or by amalgamating both materials that are to be joined. A rejecting effect can for instance be caused by an additional layer on a material of silicon or fluoride combinations. A release force (pull-off force) is thereby such a force that is necessary to separate two materials from one another (measured according to DIN 53530).

In another embodiment of the film dressing according to the present disclosure, these release characteristics are adjusted in such manner that the pull-off force which is necessary to release a cover film or paper from the polymer film to be applied is greater than the pull-off force which is necessary to release the supporting film or the supporting foils from the polymer film.

In a development of the film dressing with two supporting films, the release characteristics are adjusted in such manner that the pull-off force which is necessary to release the first supporting film from the polymer film that is to be applied is equal to the pull-off force that is necessary to release the second supporting film.

In a film dressing with two supporting films and two grip strips, the release characteristics are preferably adjusted in such manner that the pull-off force which is necessary to release the first grip strip from the second grip strip or to release the second from the first grip strip is less than the pull-off force that is necessary to release the supporting film from the polymer film that is to be applied.

In another development of the film dressing with two supporting films, the release characteristics are preferably adjusted in such manner that the pull-off force, which is necessary to release the first supporting film from the polymer film that is to be applied is greater than the pull-off force which is necessary to release the first grip strip from the second grip strip.

The adhesion of the supporting film on the polymer film is preferably only about 0.01 to about 0.5 N/25 mm, especially preferred about 0.01 to about 0.1 N/25 mm, measured according to DIN 53630. The supporting material is preferably attached directly here to the polymer film during its manufacturing process, or the polymer film is manufactured directly on the supporting material, respectively. Further, all regular methods for the film manufacturing may be applied, such as melting, spreading, extrusion or other familiar methods for manufacturing of films or foils. If necessary, the supporting material can be roughened on the coated side or be subjected to another treatment that promotes adhesion. A coating that promotes adhesion can also be beneficial.

It is in this important that the adhesion of the polymer film on the surface which is to be applied is substantially greater than the adhesion of a supporting film to the polymer film.

In a particular development of the present disclosure, it is intended that a film dressing including a polymer film with an application system is located inside of a package. It is particularly intended that the package is a sterile package.

It must be emphasized at this point that the here-referenced characteristics of the alternative developments of the inventions are not to be limited to the individual alternatives. It is rather the case that the combination of the developments and/or the combination of the individual characteristics of the alternative forms must be included in a development according to the present invention. The present invention shall be understood to be reduced just as little by the subsequent explanations of the illustrations.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

In order that the invention may be well understood, there will now be described an embodiment thereof, given by way of example, reference being made to the accompanying drawing, in which.

DETAILED DESCRIPTION

The following description is merely exemplary in nature and is not intended to limit the present disclosure, application, or uses.

Figure 1:
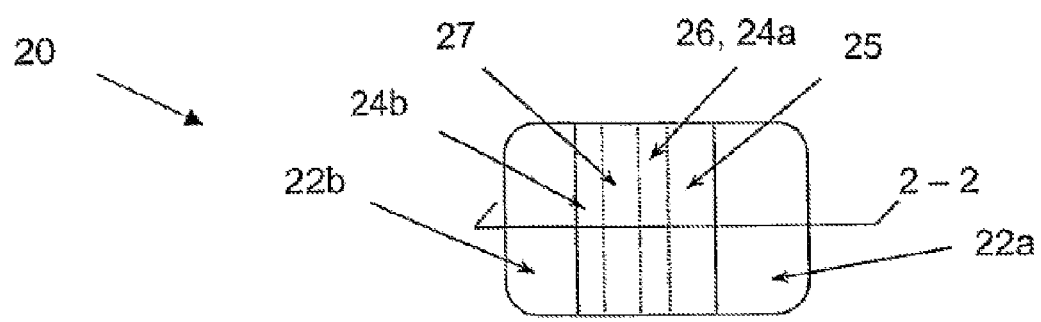
FIG. 1 is a top view of a film dressing constructed in accordance with the principles of the present disclosure.
Figure 2:
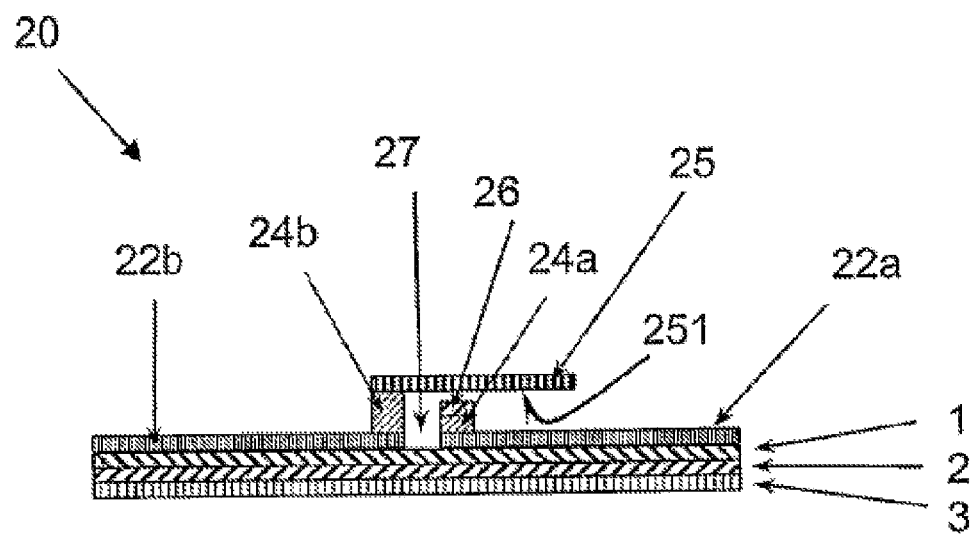
FIG. 2 is a cross-sectional view, taken along line 2-2 of FIG. 1, of the film dressing in accordance with the principles of the present disclosure.
Figure 3:
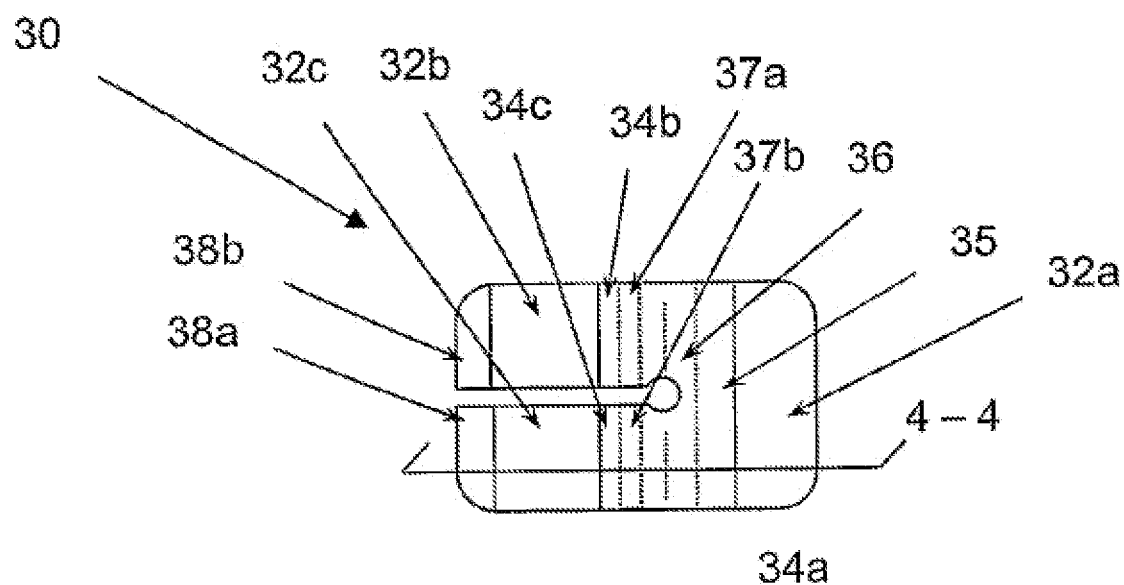
FIG. 3 is a top view of another form of a film dressing constructed in accordance with the principles of the present disclosure.
Figure 4:
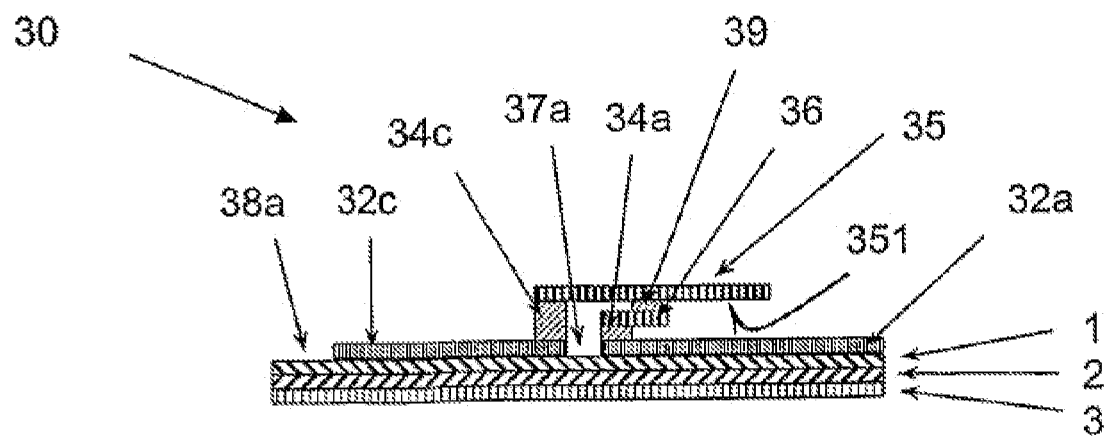
FIG. 4 is a cross-sectional view, taken along line 4-4 of FIG. 3, of another form of a film dressing in accordance with the principles of the present disclosure.

FIG. 1 and FIG. 2 illustrate a first embodiment of the present disclosure. This film dressing (20) has a rectangular basic form and comprises a polymer film (1), a continuous adhesive coating (2) that is applied on the second side of the polymer film, and a covering layer (3) that covers said adhesive. The polymer film has on its first side an application system, which comprises two supporting films (22a, 22b), two grip strips (25, 26) as well as two adhesives (24a, 24b). These two supporting films are attached to the polymer film in such a manner that said polymer film, with the exception of the non-covered area (27), is completely covered except for the supporting films. The covered area of the polymer film comprises approximately about 96% of the area of the first side of the polymer film. In this development, the first grip strip (25), which is affixed to the first supporting film (22b) by means of the first adhesive (24b) overlaps the area without a supporting film (27) as well as the second grip strip (26) which is affixed to the second supporting film (22a) by means of a second adhesive (24a). The first grip strip (25) comprises a grip surface which is formed as a rear-grasping device to enable the grip strip to be grasped. The outer portion of the grip surface protrudes peripherally as an exposed grip surface (251) beyond the second grip strip (26). This second grip strip (26) has in the illustrated embodiment no grip surface that is formed as a rear grasping device. This is, however, as illustrated in FIGS. 3 and 4 in the case of a patch used to affix hypodermic needles also possible and beneficial in order to improve the grasping of the second grip strip (26). Due to the fact that only one grip strip can be grasped and seen by the user, a sequence is pre-determined for the removal of both of the supporting films.

FIG. 3 and FIG. 4 illustrate another form of a film dressing (30) in accordance with the principles of the present disclosure. This film dressing can be used as a patch to affix hypodermic needles or catheters. The film dressing comprises a rectangular basic form, whereas its short side exhibits an indentation that is positioned parallel to the long side. This indentation gives the film dressing two areas that are independent from one another which are attached through a third area and which, for instance during the positioning of a hypodermic needle, are always on one side of the hypodermic needle affixed to one surface. The film dressing exhibits a polymer film (1), an acrylate-adhesive layer (2) and a covering layer (3) that covers the adhesive layer. An application system is positioned on the first side of the polymer film, which is positioned away from the adhesive layer. This application system comprises two grip strips (35, 36) which are affixed on three supporting films (32a, 32b, 32c) by means of three adhesives (34a, 34b, 35c). The first grip strip (35) is allocated to the first supporting film (32c) as well as to the second supporting film (32b) and thus formed to it. Both of these supporting films (32c, 32b) can thus be removed in the same grasp. The first grip strip (35) overlaps the central areas of the polymer film which are not covered by supporting films (37a, 37b), as well as the second grip strip (36). The outer portion of the grip surface protrudes as an exposed grip surface (351) peripherally beyond the second grip strip (26), whereas a sequence for the removal of said second grip strip (26) has been determined here as well.

The supporting films cover a total surface of the polymer film which is equal to about 92% of the surface of the first side of the polymer film, since in addition to the central areas (37a, 37b), which are not covered by supporting films, a supporting film is not positioned in either of the two marginal areas (38a, 38b) as well. These peripheral areas without supporting films can be used for a first positioning after removal of the cover layer. FIG. 4 also illustrates an activation device (39) between the two grip strips. This activation device (39) as well as the adhesive for the positioning of the grip strip (36) to the supporting film (32a) is not illustrated in FIG. 3. This activation device (39) is a double-sided adhesive tape which comprises a higher adhesive strength for the first grip strip (35) than for the second grip strip (36). This causes during the removal of the supporting films (32b, 32c) by means of the first grip strip (35) to lift up the underlying second grip strip (36) before the adhesive force between the first grip strip (35) and the activation device (39) can be overcome. The second grip strip (36) is thus easier to grasp in the next step when removing the supporting film (32a).

Figure 5A:
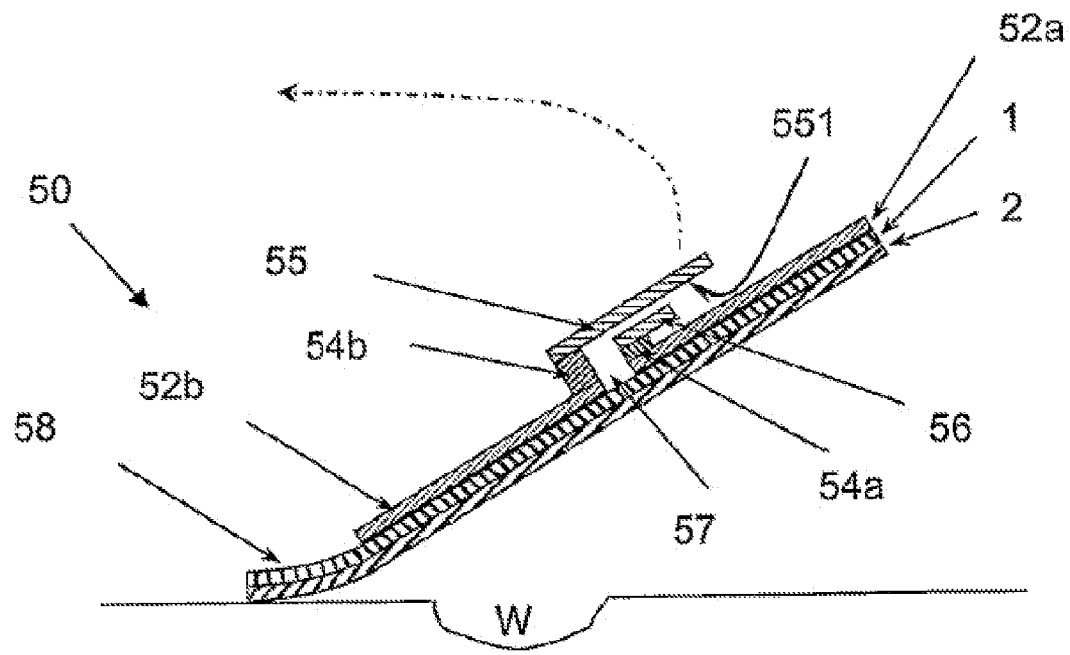
FIGS. 5 a-c are cross-sectional views of a film dressing being applied in accordance with the principles of the present disclosure.
Figure 5B:
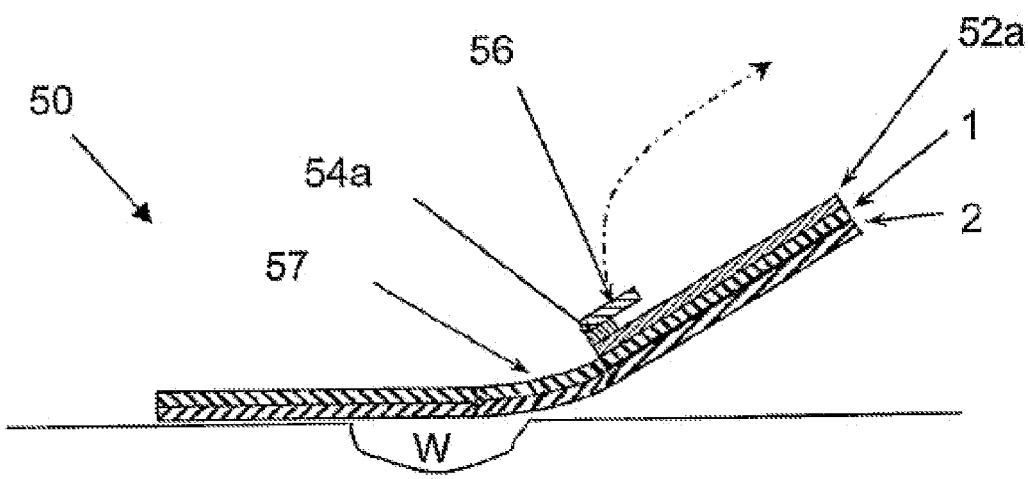
Figure 5C:
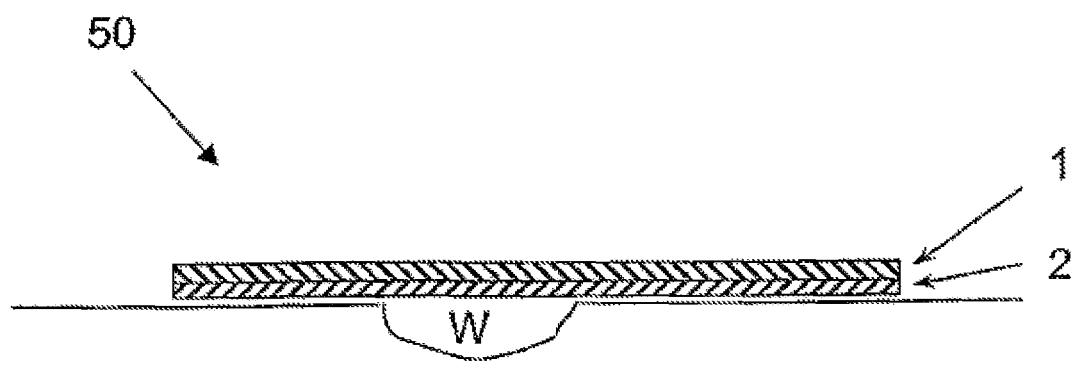

FIGS. 5a to 5c illustrate the application of a film dressing according to the present disclosure with two areas without supporting films following the removal of the covering layer (3) from the adhesive layer (2). In order to apply, for instance, a film dressing (30, 50) above a wound (W), as shown in FIGS. 5a to 5c, a first peripheral area without supporting films (38a, 38b, 58) can therefore be positioned to an area that borders the wound (W). This is perfectly possible due to the high flexibility of the polymer film without the supporting film. In an additional step, the user can then with help of the predetermined configuration of the grip strips (35, 36, 55, 56), which are affixed to the individual supporting films by means of adhesives (34a, 34b, 34c, 54a, 54b) place the polymer film (1) which is to be applied directly above the wound. Due to the additional area (37a, 37b, 57) that is not covered by supporting films, the film dressing exhibits some kind of joint which allows for wrinkle-free application. The supporting films (32a, 32b, 32c, 52a, 52b) can be successively removed during the application or following the application of the polymer film, whereas the first grip strip (33, 55) can initially be grasped by its exposed grip surface (351, 551) and the first supporting film (32b, 32c, 52b) is then removed first.

Embodiment 1

The film dressing comprises a rectangular basic form with an edge length of about 57× about 80 mm (contact surface about 45.6 cm$^2$). It comprises a transparent polyether urethane film, which on the side that is positioned towards the body is coated with an acrylate-based hydrogel adhesive. The adhesive is affixed continuously in the amount of about 35 g/m$^2$ onto the about 25 μm thick polymer film (measured with a test pressure of about 0.5 kPa). The polymer film together with the adhesive comprises a condensation permeability of about 2,600 g/m$^2$/24 hrs. (measured according to DIN EN 13726, with the difference that after about 4 hrs. the measurement period was terminated and the determined result is extrapolated for about 24 hrs.). Such a polymer film is available under the trade name Inspire 6200 from the company InteliCoat Technologies, Wrexham Industrial Estate, Wrexham LL13 9UF, UK. The adhesive side of this polymer film is available from the company Maria Soell GmbH & Co. KG, Frankenstrasse 45, D-63667 Nidda-Eichelsdorf, with a siliconized cover paper and covered under the trade name Separacon 980-60. The other side of the polymer film, which during the application is positioned away from the body, comprises an application system which consists of two supporting films that each has one grip strip. The supporting films are, as illustrated in FIG. 1 and FIG. 2, positioned on the polymer film. The film dressing at hand additionally realizes a peripheral area, which is not covered by a supporting film or grip strip. This additional peripheral area without a supporting film is positioned on the short side of the rectangle and comprises an equal width of about 5 mm. Both of the supporting films are equal in size and comprise an edge length of about 57× about 36 mm (contact area: 2×20.5 cm$^2$=about 41.0 cm$^2$). The distance of both films is about 3 mm in each point of their parallel edges that are of equal length. This results for both supporting films in a combined contact area of about 90% in respect of the surface of the first polymer film. The supporting films are manufactured of a about 30 μm thick polyester film (measured at a test pressure of about 0.5 kPa). A grip strip is affixed onto each supporting film with an acrylate adhesive. The grip strips together comprise a configuration, as illustrated in FIG. 4, whereas the first grip strip, which is sketched with reference mark (35), has a size of about 57× about 39 mm and is throughout the entire width (57 mm) attached to the respective supporting film. The second grip strip, which is illustrated with reference (36), comprises a size of about 57× about 22 mm. Both grip strips are each attached to the respective supporting film through a about 5 mm wide adhesive connective strip and are manufactured from a 20 μm thick transparent polyester film. The first grip strip thus has a strip surface with an equally formed width of about 34 mm. The size of the grip surface of the first grip strip comprises about 19.4 cm$^2$. The equally shaped width of the grip surface of the second grip strip comprises about 17 mm. The size of the grip surface of the second grip strip thus comprises about 9.7 cm$^2$. The equally shaped width of that portion which protrudes beyond the second grip strip of the first grip surface that is the width of the exposed grip surface of the first grip strip measures about 9 mm. The size of the exposed grip surface thus comprises about 5.1 cm$^2$.

Embodiment 2

The film dressing comprises a rectangular basic form with an edge length of about 57× about 80 mm (contact surface about 45.6 cm$^2$). It comprises a transparent polyether urethane film which on the side that is positioned towards the body is coated with a pressure sensitive acrylate-based adhesive. The adhesive is affixed continuously in the amount of about 25 g/m$^2$ onto about 30 μm thick polymer film (measured with a test pressure of about 0.5 kPa). The polymer film together with the adhesive comprises a condensation permeability of about 1,200 g/m$^2$/24 hrs. (measured according to DIN EN 13726). Such a polymer film is available under the trade name Inspire 1305 from the company InteliCoat Technologies, Wrexham Industrial Estate, Wrexham LL13 9UF, UK. The adhesive side of this polymer film is available from the company Maria Soell GmbH & Co. KG, Frankenstrasse 45, D-63667 Nidda-Eichelsdorf, with a siliconized cover paper and covered under the trade name Separacon 980-60. The other side of the polymer film, which during the application is positioned away from the body, comprises an application system which consists of two supporting films that each has one grip strip. The supporting films, as illustrated in FIG. 1 and FIG. 2, are positioned on the polymer film. The film dressing at hand additionally realizes a peripheral area which is not covered by a supporting film or grip strip. This additional peripheral area without a supporting film is positioned on the short side of the rectangle and comprises an equal width of about 5 mm. Both of the supporting films are equal in size and comprise an edge length of about 57× about 36 mm (contact area: 2×20.5 cm$^2$=about 41.0 cm$^2$). The distance of both films is about 3 mm in each point of their parallel edges that are of equal length. This results for both supporting films in a combined contact area of about 90% in respect of the surface of the first polymer film. The supporting films are manufactured of a 30 μm thick polyester film (measured at a test pressure of about 0.5 kPa). A grip strip is affixed onto each supporting film with an acrylate adhesive. The grip strips in a cross-sectional view comprise a configuration, as illustrated in FIG. 4, whereas the first grip strip, which is sketched with reference mark (35), has a size of about 57× about 39 mm and is throughout the entire width (57 mm) attached to the respective supporting film. The second grip strip, which is illustrated with reference mark (36), comprises a size of about 57× about 22 mm. Both grip strips are each attached to the respective supporting film through a 5 mm wide adhesive connective strip and are manufactured from a 20 μm thick transparent polyester film. The first grip strip thus has a strip surface with an equally formed width of 3 about 4 mm. The size of the grip surface of the first grip strip comprises about 19.4 cm².

The equally shaped width of the grip surface of the second grip strip comprises about 17 mm. The size of the grip surface of the second grip strip thus comprises about 9.7 cm². The equally shaped width of that portion which protrudes beyond the second grip strip of the first grip surface that is the width of the exposed grip surface of the first grip strip measures about 9 m. The size of the exposed grip surface thus comprises about 5.1 cm².

The release characteristics of the materials used in this embodiment 2 were determined on about 60× about 80 mm test sections according to the method described in DIN 53 530. The tests were completed with a pull-off velocity of about 300 mm/min. The silicon paper in respect of the polymer film therefore exhibits a release force of about 0.77 N/25 mm, whereas the supporting film in respect of the polymer film exhibits a release force of about 0.09 N/25 mm. The release characteristics of this film dressing are hence adjusted such that the pull-off force which is necessary to release a cover film from the polymer film that is to be applied is greater than the pull-off force which is necessary to separate the supporting film or the supporting films from the polymer film.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. A film dressing comprising a polymer film having a first side and a second side, an adhesive applied on the second side, and a covering layer on the second side that covers the adhesive, and an application system for permitting an improved ease of use of said film dressing, the polymer film defining an indentation and the application system being located on the first side of the polymer film and comprising at least one first grip strip and at least one second grip strip, and at least one first supporting film positioned on one side of the indentation, a second supporting film positioned on another side of the indentation, and a third supporting film, wherein the first supporting film is offset from the second and third supporting films such that the first supporting film does not overlap the second and third supporting films, characterized in that the at least one first grip strip is on the first supporting film and the second supporting film, and the at least one second grip strip is on the third supporting film, wherein the at least one first grip strip is affixed to the first supporting film and the at least one second supporting film by adhesives, and the at least one second grip strip is affixed to the third supporting film by an adhesive, in which at least the at least one first grip strip comprises a grip surface that enables the at least one first grip strip to be grasped and the at least one first grip strip at least partially overlaps the at least one second grip strip.

2. The film dressing according to claim 1, characterized in that the second side of the polymer film is coated with an adhesive material, and the adhesive material is covered with a release film or paper.

3. The film dressing according to claim 2, characterized in that the second side of the polymer film is continuously coated with the adhesive material.

4. The film dressing according to claim 1, characterized in that the at least one first grip strip completely overlaps the at least one second grip strip and comprises an exposed grip surface of at least 2 cm².

5. The film dressing according to claim 1, characterized in that the polymer film comprises at least an area without any of the first, the second, or the third supporting films.

6. The film dressing according to claim 1, characterized in that at least one of the at least one first grip strip and the at least one second grip strip overlaps at least partially a first area without any of the first, the second, or the third supporting films.

7. The film dressing according to claim 1, characterized in that the application system and the polymer film are the same size.

8. The film dressing according to claim 1, characterized in that the polymer film comprises a peripheral area without any of the first, the second, or the third supporting films.

9. The film dressing according to claim 1, characterized in that a first area without the any of the first, the second, or the third supporting films of the polymer film is positioned between the first and the second supporting films.

10. The film dressing according to claim 1, characterized in that the polymer film comprises at least two areas without any of the first, the second, or the third supporting films that are separated from one another.

11. The film dressing according to claim 1, characterized in that the first, the second, and the third supporting films and the at least one first grip strip and the at least one second grip strip are comprised of identical materials.

12. The film dressing according to claim 1, characterized in that the at least one first grip strip is more rigid than the at least one second grip strip.

13. The film dressing according to claim 1, characterized in that a wound pad is attached to the second side of the polymer film.

14. The film dressing according to claim 1, characterized in that a layer that promotes the healing of a wound is attached to the second side of the polymer film.

15. The film dressing according to claim 1, characterized in that the polymer film is selected from a group consisting of a polyurethane film, a polyester urethane film, and a polyether urethane film.

16. The film dressing according to claim 1 further comprising an activation device positioned between the at least one first grip strip and the at least one second grip strip.

* * * * *